US006197011B1

(12) United States Patent
Freitas et al.

(10) Patent No.: US 6,197,011 B1
(45) Date of Patent: Mar. 6, 2001

(54) MALE INCONTINENCE DIAPER

(76) Inventors: Evelyn J. Freitas; Walter R. Freitas, both of P.O. Box 479, Grass Valley, CA (US) 95945

( * ) Notice: Subject to any disclaimer, the term of this patent is extended or adjusted under 35 U.S.C. 154(b) by 0 days.

(21) Appl. No.: 09/164,635

(22) Filed: Oct. 1, 1998

(51) Int. Cl.[7] .................................................. A61F 13/15
(52) U.S. Cl. .............................. 604/385.03; 604/385.09; 604/385.24; 604/392
(58) Field of Search ........................ 604/385.03, 385.09, 604/327, 340–47, 349, 351, 353, 385.19; 602/67–73; 2/403, 405

(56) References Cited

U.S. PATENT DOCUMENTS

| | | | | |
|---|---|---|---|---|
| 375,846 | * | 1/1888 | Ware | 602/70 |
| 508,229 | * | 11/1893 | Marcy | 602/73 |
| 713,318 | * | 11/1902 | Lovis | 602/70 |
| 860,584 | * | 7/1907 | Teufel | 602/70 |
| 1,641,094 | * | 8/1927 | Peterkin | 602/71 |
| 1,672,748 | * | 6/1928 | Bruner | 604/351 |
| 2,439,683 | * | 4/1948 | Broderick | 604/353 |
| 5,234,423 | * | 8/1993 | Alemany | 604/389 |
| 5,383,867 | * | 1/1995 | Klinger | 604/398 |
| 5,569,229 | * | 10/1996 | Rogers | 604/385.09 |
| 5,618,279 | * | 4/1997 | Pudlo | 604/347 |
| 5,735,837 | * | 4/1998 | Ishikawa | 604/349 |
| 5,984,910 | * | 11/1999 | Berke | 604/385.1 |

FOREIGN PATENT DOCUMENTS

| 523140 | * | 4/1931 | (DE) | 604/398 |
|---|---|---|---|---|
| 87/07136 | * | 12/1987 | (WO) . | |

* cited by examiner

*Primary Examiner*—John G. Weiss
*Assistant Examiner*—K. M. Reichle

(57) ABSTRACT

A male incontinence diaper for absorbing urine from a male user. The male incontinence diaper includes a back panel with a hole therethrough extending between the front and back faces of the back panel. A front flap is coupled to back panel along the side edges and the bottom edge of the back panel to cover the hole of the back panel. An elongate flexible belt strap is coupled to the back panel adjacent the top edge of the back panel.

9 Claims, 2 Drawing Sheets

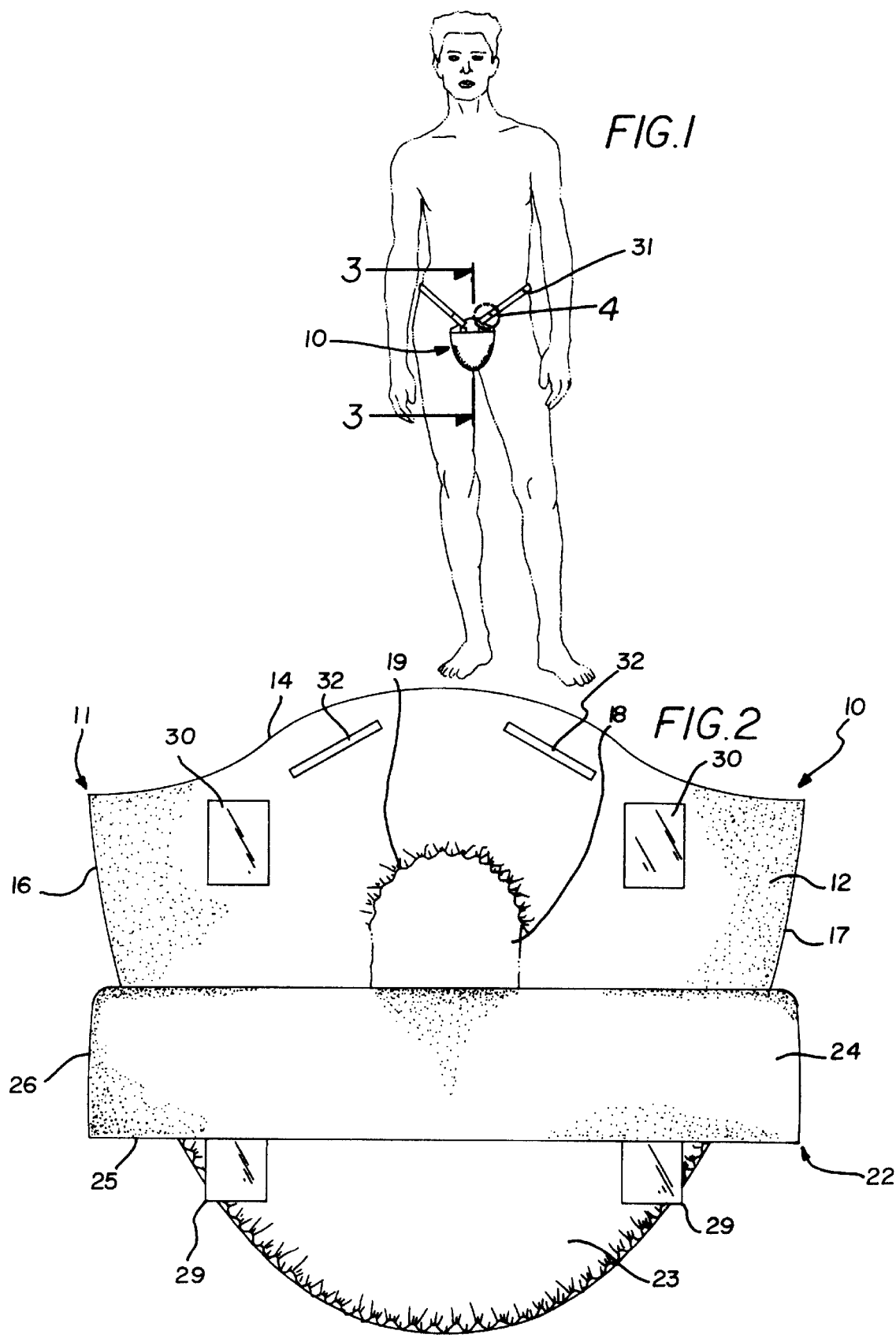

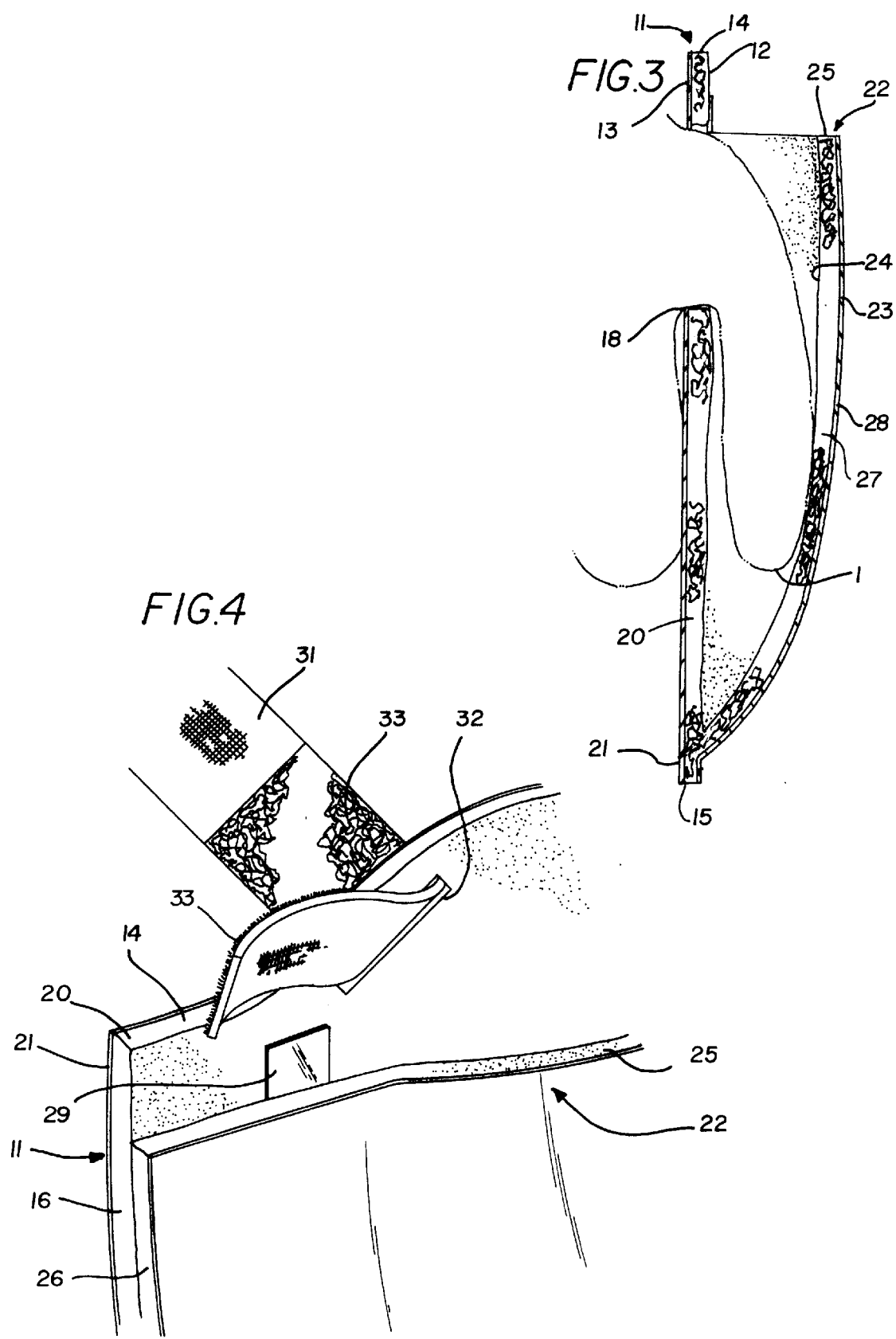

MALE INCONTINENCE DIAPER

BACKGROUND OF THE INVENTION

1. Field of the Invention

The present invention relates to incontinence diapers and more particularly pertains to a new male incontinence diaper for absorbing urine from a male user.

2. Description of the Prior Art

The use of incontinence diapers is known in the prior art. Known prior art includes U.S. Pat. No. 5,074,853; U.S. Pat. No. 5,531,732; U.S. Pat. No. 4,944,733; U.S. Pat. No. 4,338,939; U.S. Pat. No. 3,162,196; and U.S. Pat. No. 2,969,065.

While these devices fulfill their respective, particular objectives and requirements, the aforementioned patents do not disclose a new male incontinence diaper. The inventive device includes a back panel with a hole therethrough extending between the front and back faces of the back panel. A front flap is coupled to back panel along the side edges and the bottom edge of the back panel to cover the hole of the back panel. An elongate flexible belt strap is coupled to the back panel adjacent the top edge of the back panel.

In these respects, the male incontinence diaper according to the present invention substantially departs from the conventional concepts and designs of the prior art, and in so doing provides an apparatus primarily developed for the purpose of absorbing urine from a male user.

SUMMARY OF THE INVENTION

In view of the foregoing disadvantages inherent in the known types of incontinence diapers now present in the prior art, the present invention provides a new male incontinence diaper construction wherein the same can be utilized for absorbing urine from a male user.

To attain this, the present invention generally comprises a back panel with a hole therethrough extending between the front and back faces of the back panel. A front flap is coupled to back panel along the side edges and the bottom edge of the back panel to cover the hole of the back panel. An elongate flexible belt strap is coupled to the back panel adjacent the top edge of the back panel.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is another object of the present invention to provide a new male incontinence diaper which may be easily and efficiently manufactured and marketed.

It is a further object of the present invention to provide a new male incontinence diaper which is of a durable and reliable construction.

An even further object of the present invention is to provide a new male incontinence diaper which is susceptible of a low cost of manufacture with regard to both materials and labor, and which accordingly is then susceptible of low prices of sale to the consuming public, thereby making such male incontinence diaper economically available to the buying public.

Still yet another object of the present invention is to provide a new male incontinence diaper which provides in the apparatuses and methods of the prior art some of the advantages thereof, while simultaneously overcoming some of the disadvantages normally associated therewith.

Still another object of the present invention is to provide a new male incontinence diaper for absorbing urine from a male user.

Yet another object of the present invention is to provide a new male incontinence diaper which includes a back panel with a hole therethrough extending between the front and back faces of the back panel. A front flap is coupled to back panel along the side edges and the bottom edge of the back panel to cover the hole of the back panel. An elongate flexible belt strap is coupled to the back panel adjacent the top edge of the back panel.

Still yet another object of the present invention is to provide a new male incontinence diaper that prevents urine from running down the legs of a wearer unlike traditionally configured incontinence diapers.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a schematic front side view of a new male incontinence diaper in use according to the present invention.

FIG. 2 is a schematic front side view of the present invention.

FIG. 3 is a schematic cross sectional view of the present invention taken along line 3—3 of FIG. 1.

FIG. 4 is an enlarged schematic partial perspective view of the present invention as indicated by area 4 of FIG. 1.

DESCRIPTION OF THE PREFERRED EMBODIMENT

With reference now to the drawings, and in particular to FIGS. 1 through 4 thereof, a new male incontinence diaper embodying the principles and concepts of the present invention and generally designated by the reference numeral 10 will be described.

As best illustrated in FIGS. 1 through 4, the male incontinence diaper 10 generally comprises a back panel 11 with a hole 18 therethrough extending between the front and back faces 12,13 of the back panel 11. A front flap 22 is coupled to back panel 11 along the side edges 16,17 and the bottom edge 15 of the back panel 11 to cover the hole 18 of the back panel 11. An elongate flexible belt strap 31 is coupled to the back panel 11 adjacent the top edge 14 of the back panel 11.

In closer detail, the back panel 11 has front and back faces 12,13, arcuate top and bottom edges 14,15 and a pair of generally straight side edges 16,17 extending between the top and bottom edges 14,15 of the back panel 11. As illustrated in FIGS. 1 and 3, the back face 13 of the back panel 11 is designed for positioning against the genitalia region of a wearer to substantially cover the genitalia region of the wearer. The back panel 11 has a hole 18 therethrough extending between the front and back faces 12,13 of the back panel 11. The hole 18 of the back panel 11 is designed for extending the penis 1 of a wearer therethrough as illustrated in FIG. 3. The hole 18 of the back panel 11 preferably has a generally rounded oblong outer periphery for providing added comfort to the wearer. The back panel 11 has an resiliently elastic band 19 extending along the outer periphery of the hole 18 of the back panel 11, the elastic band 19 is designed for constricting the outer periphery of the hole 18 of the back panel 11 around the circumference of the penis 1 of a wearer extended through the hole 18 of the back panel 11 to prevent urine from passing through the hole 18.

With reference to FIG. 3, the back panel 11 comprises a fluid absorbing fabric material 20 such as a cotton fluid absorbent material for absorbing urine from a wearer. The back panel 11 also has a water impermeable layer 21 provided on the back face 13 of the back panel 11 for preventing passage of fluids through the water impermeable layer of the back panel 11. The water impermeable layer of the back panel 11 is preferably substantially coextensive with back face 13 of the back panel 11.

The top edge 14 of the back panel 11 preferably has a generally camel-back configuration for the comfort of the wearer with a convex region interposed between a pair of concave regions. Each of the concave regions of the top edge 14 of the back panel 11 is positioned adjacent an associated side edge 16,17 of the back panel 11. The bottom edge 15 of the back panel 11 preferably has a generally semi-circular configuration with an outwardly extending convexity for the comfort of the wearer. The side edges 16,17 of the back panel 11 converge together in a direction from the top edge 14 of the back panel 11 towards the bottom edge 15 of the back panel 11 such that the back panel 11 has a width defined between the side edges 16,17 of the back panel 11 greater adjacent the top edge 14 of the back panel 11 than adjacent the bottom edge 15 of the back panel 11. In an ideal illustrative embodiment, the width of the back panel 11 tapers from about 6 inches at the top edge 14 of the back panel 11 to about 3 inches adjacent the bottom edge 15 of the back panel 11. In this ideal illustrative embodiment, each of the side edges 16,17 of the back panel 11 has a length of about 12 inches between the top and bottom edges of the back panel 11 so that the back panel substantially covers the genitalia region of the wearer.

The front flap 22 has front and back faces 23,24, a generally straight upper edge 25 and a generally U-shaped arcuate lower edge 26. The lower edge 26 of the front flap 22 is coupled to back panel 11 along the side edges 16,17 and the bottom edge 15 of the back panel 11 with the back face 24 of the front flap 22 facing the front face 12 of the back panel 11. Together, the back face 24 of the front flap 22 and the front face 12 of the back panel 11 define a pocket designed for receiving a penis 1 of a wearer extended through the hole 18 of the back panel 11.

Like the back panel, the front flap 22 comprises a fluid absorbing fabric material 27 such as a cotton fluid absorbent material for absorbing urine from a wearer. The front flap 22 also has a water impermeable layer 28 provided on the front face 23 of the front flap 22 for preventing passage of fluids through the water impermeable layer of the front flap 22. Ideally, the water impermeable layer of the front flap 22 is substantially coextensive with front face 23 of the front flap 22.

As illustrated in FIG. 2, the upper edge 25 of the front flap 22 is attached to the front face 12 of the back panel 11. Preferably, a pair of adhesive strips 29 attaches the upper edge 25 of the front flap 22 to the front face 12 of the back panel 11. The adhesive strips 29 are provided on the front flap 22 and outwardly extend from the upper edge 25 of the front flap 22 to provide an exposed portion designed for attachment to the front face 12 of the back panel 11. Ideally, the back panel 11 has a pair of generally smooth surfaced regions 30 provided on the front face 12 of the back panel 11. The adhesive strips 29 are adhesively attachable to the smooth surfaced regions 30 of the back panel 11. In use, the smooth surfaced regions 30 of the back panel 11 permit peelable detachment of the adhesive strips 29 from the front face 12 of the back panel 11 without significant loss of the adhesive material on the adhesive strips 29 so that the adhesive strips 29 are repeatedly re-attachable on to the smooth surfaced regions 30.

As illustrated in FIG. 1 and 4, the elongate flexible belt strap 31 has a pair of opposite ends coupled to the back panel 11 adjacent the top edge 14 of the back panel 1. The flexible belt strap 31 is designed for wrapping around a waist of a wearer to secure the back panel 11 to a wearer in the proper position over the genitalia region of the wearer. Preferably, the back panel 11 has a pair of slits 32 therethrough extending between the front and back faces 12,13 of the back panel 11. The slits 32 are positioned adjacent the top edge 14 of the back panel 11. One of the ends of the flexible belt strap 31 is looped through one of the slits and the other end of the flexible belt strap is looped through the other slit to attach the ends of the flexible belt strap 31 to the back panel 11. As illustrated in FIG. 4, ideally, each end of the flexible belt strap 31 is secured to an adjacent portion of the flexible belt strap 31 by a hook and loop fastener 33 after is looped through the associated slit. The flexible belt strap 31 has a length defined between the ends of the flexible belt strap 31. Preferably, the flexible belt strap 31 comprises a resiliently elastic material to permit resilient stretching of the flexible belt strap 31 along the length of the flexible belt strap 31.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. An incontinence diaper, comprising:

a back panel having front and back faces, top and bottom edges and a pair of side edges extending between said top and bottom edges of said back panel;

said back panel having a hole therethrough extending between said front and back faces of said back panel;

a front flap having front and back faces, an upper edge and a lower edge, said lower edge of said front flap being coupled to back panel along said side edges and said bottom edge of said back panel, said back face of said front flap facing said front face of said back panel;

an elongate flexible belt strap having a pair of opposite ends coupled to said back panel adjacent said top edge of said back panel; and wherein said top edge of said back panel has a generally camel-back configuration having a convex region interposed between a pair of concave regions, each of said concave regions of said top edge of said back panel being positioned adjacent an associated side edge of said back panel, and wherein said bottom edge of said back panel has a generally semi-circular configuration having an outwardly extending convexity.

2. The incontinence diaper of claim 1, wherein said hole of said back panel has an outer periphery, and wherein said back panel has an resiliently elastic band extending along said outer periphery of said hole of said back panel.

3. The incontinence diaper of claim 1, wherein said back panel comprises a fluid absorbing material, wherein said back panel has a water impermeable layer provided on said back face of said back panel for preventing passage of fluids through said back panel, wherein said front flap comprises a fluid absorbing material, and wherein said front flap has a water impermeable layer provided on said front face of said front flap for preventing passage of fluids through said front flap.

4. The incontinence diaper of claim 1, wherein said side edges of said back panel converge together in a direction from said top edge of said back panel towards said bottom edge of said back panel such that said back panel has a width defined between said side edges of said back panel greater adjacent said top edge of said back panel than adjacent said bottom edge of said back panel.

5. The incontinence diaper of claim 1, wherein said upper edge of said front flap is attached to said front face of said back panel.

6. The incontinence diaper of claim 5, wherein a pair of adhesive strips attaches said upper edge of said front flap to said front face of said back panel, said adhesive strips being, provided on said front flap and outwardly extending from said upper edge of said front flap.

7. The incontinence diaper of claim 6, wherein said back panel has a pair of generally smooth surfaced regions provided on said front face of said back panel, said adhesive strips being adhesively attachable to said smooth surfaced regions of said back panel, said smooth surfaced regions of said back panel permitting peelable detachment of said adhesive strips from said front face of said back panel without significant loss of the adhesive material on the adhesive strips so that the adhesive strips are repeatedly re-attachable onto the smooth surfaced regions.

8. The incontinence diaper of claim 1, wherein said back panel has a pair of slits therethrough extending between said front and back faces of said back panel, said slits being positioned adjacent said top edge of said back panel, one of said ends of said flexible belt strap being looped through one of said slits and another of said ends of said flexible belt strap being looped through the other of said slits to attach said ends of said flexible belt strap to said back panel.

9. An incontinence diaper, comprising:

a back panel having front and back faces, arcuate top and bottom edges and a pair of generally straight side edges extending between said top and bottom edges of sad back panel;

said back face of said back panel being adapted for positioning against the genitalia region of a wearer to substantially cover the genitalia region of a wearer;

said back panel having a hole therethrough extending between said front and back faces of said back panel, said hole of said back panel being adapted for extending a penis of the wearer therethrough, said hole of said back panel having a generally rounded oblong outer periphery;

said back panel having an resiliently elastic band extending along said outer periphery of said hole of said back panel, said elastic band being adapted for constricting said outer periphery of said hole of said back panel around the circumference of a penis of the wearer extended through said hole of said back panel;

said back panel comprising a fluid absorbing material for absorbing urine from the wearer;

said back panel having a water impermeable layer provided on said back face of said back panel for preventing passage of fluids through said back panel, said water impermeable layer of said back panel being substantially coextensive with back face of said back panel;

said top edge of said back panel having a generally camel back configuration having a convex region interposed between a pair of concave regions, each of said concave regions of said top edge of said back panel being positioned adjacent an associated side edge of said back panel;

said bottom edge of said back panel having a generally semi circular configuration having an outwardly extending convexity;

said side edges of said back panel converging together in a direction from said top edge of said back panel towards said bottom edge of said back panel such that said back panel has a width defined between said side edges of said back panel greater adjacent said top edge of said back panel than adjacent said bottom edge of said back panel;

a front flap having front and back faces, a generally straight upper edge and a generally U-shaped arcuate lower edge, said lower edge of said front flap being coupled to back panel along said side edges and said bottom edge of said back panel, said back face of said front flap facing said front face of said back panel;

said back face of said front flap and said front face of said back panel defining a pocket adapted for receiving a penis of the wearer extended through said hole of said back panel;

said front flap comprising a fluid absorbing material for absorbing urine from the wearer;

said front flap having a water impermeable layer provided on said front face of said front flap for preventing passage of fluids through said front flap, said water impermeable layer of said front flap being substantially coextensive with front face of said front flap;

said upper edge of said front flap being attached to said front face of said back panel;

wherein a pair of adhesive strips attaches said upper edge of said front flap to said front face of said back panel, said adhesive strips being provided on said front flap and outwardly extending from said upper edge of said front flap;

an elongate flexible belt strap having a pair of opposite ends coupled to said back panel adjacent said top edge of said back panel, said flexible belt strap being adapted for wrapping around a waist of the wearer to secure said back panel to the wearer;

said back panel having a pair of slits therethrough extending between said front and back faces of said back panel, said slits being positioned adjacent said top edge of said back panel;

one of said ends of said flexible belt strap being looped through one of said slits and the other of said ends of said flexible belt strap being looped through another of said slits to attach said ends of said flexible belt strap to said back panel; and said flexible belt strap having a length defined between said ends of said flexible belt strap, wherein said flexible belt strap comprises a resiliently elastic material to permit resilient stretching of said flexible belt strap along said length of said flexible belt strap.

* * * * *